(12) United States Patent
Cooke

(10) Patent No.: US 9,870,515 B2
(45) Date of Patent: Jan. 16, 2018

(54) IDENTIFICATION SYSTEM AND METHOD

(71) Applicant: EMPIRE TECHNOLOGY DEVELOPMENT LLC, Wilmington, DE (US)

(72) Inventor: Cameron Cooke, Sydney (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 5 days.

(21) Appl. No.: 15/037,329

(22) PCT Filed: Apr. 5, 2014

(86) PCT No.: PCT/US2014/033106
§ 371 (c)(1),
(2) Date: May 18, 2016

(87) PCT Pub. No.: WO2015/152946
PCT Pub. Date: Oct. 8, 2015

(65) Prior Publication Data
US 2016/0307064 A1   Oct. 20, 2016

(51) Int. Cl.
*G06K 9/00* (2006.01)
*G06K 9/46* (2006.01)
(Continued)

(52) U.S. Cl.
CPC .......... *G06K 9/4661* (2013.01); *A61B 5/0075* (2013.01); *A61B 5/7203* (2013.01);
(Continued)

(58) Field of Classification Search
USPC .......................... 382/103, 181–231, 128–134
See application file for complete search history.

(56) References Cited

U.S. PATENT DOCUMENTS

| 6,690,466 B2 | 2/2004 | Miller et al. |
| 7,342,658 B2 | 3/2008 | Kowarz et al. |

(Continued)

FOREIGN PATENT DOCUMENTS

EP  2019299 B1  4/2011

OTHER PUBLICATIONS

"Astrium," Wikipedia, accessed at http://web.archive.org/web/20140318233151/http://en.wikipedia.org/wiki/Astrium, last modified on Jan. 28, 2014, pp. 1-3.

(Continued)

*Primary Examiner* — Alex Liew
(74) *Attorney, Agent, or Firm* — Turk IP Law, LLC

(57) ABSTRACT

A system to identity at least a property of a substance located in an object, or located on a surface of the object, is generally described. The system may include an electromagnetic radiation (EMR) source arranged to selectively emit EMR at more than one wavelength to illuminate the surface of the object. The system may include an EMR sensor arranged to sense EMR returned from the surface and to use the returned EMR to provide an output signal that represents an image taken of the surface, the image including a plurality of pixels. The system may include a processor system arranged to compare information that is indicative of the output signal of the EMR sensor with reference information indicative of the property of the substance. The processor system may be arranged to select a first wavelength to illuminate the surface by the EMR source, and subsequently select at least one further wavelength based on whether the information concerning the property is obtained as a result of use of a preceding wavelength. The processor system may be arranged to compensate fur an influence of ambient light on the at least one surface, and may be arranged to compensate for motion of the object relative to the EMR sensor.

19 Claims, 3 Drawing Sheets

(51) Int. Cl.
| | |
|---|---|
| G01N 33/00 | (2006.01) |
| G06T 7/00 | (2017.01) |
| A61B 5/00 | (2006.01) |
| H04N 5/225 | (2006.01) |
| H04N 5/372 | (2011.01) |
| H04N 5/374 | (2011.01) |
| G06T 7/246 | (2017.01) |

(52) U.S. Cl.
 CPC .......... *A61B 5/7207* (2013.01); *G01N 33/00* (2013.01); *G06T 7/001* (2013.01); *G06T 7/248* (2017.01); *H04N 5/2256* (2013.01); *H04N 5/372* (2013.01); *H04N 5/374* (2013.01); *G06K 2009/4657* (2013.01); *G06T 2207/10152* (2013.01)

(56) References Cited

U.S. PATENT DOCUMENTS

| 7,835,002 | B2 | 11/2010 | Muhammed et al. | |
|---|---|---|---|---|
| 8,571,325 | B1 | 10/2013 | Robinson et al. | |
| 2001/0046309 | A1* | 11/2001 | Kamei | G06T 7/254 382/103 |
| 2002/0092989 | A1 | 7/2002 | Toomey | |
| 2003/0135122 | A1* | 7/2003 | Bambot | A61B 5/0071 600/476 |
| 2004/0208373 | A1* | 10/2004 | Aoki | G06K 9/2018 382/191 |
| 2007/0024946 | A1 | 2/2007 | Panasyuk et al. | |
| 2010/0056928 | A1* | 3/2010 | Zuzak | A61B 5/0071 600/476 |
| 2012/0134582 | A1 | 5/2012 | Treado et al. | |
| 2012/0250025 | A1 | 10/2012 | Moshe et al. | |
| 2012/0307056 | A1 | 12/2012 | Zuzak et al. | |
| 2013/0236073 | A1 | 9/2013 | Piratla et al. | |

OTHER PUBLICATIONS

"Chemical imaging," Wikipedia, accessed at http://web.archive.org/web/20140316030457/http://en.wikipedia.org/wiki/Chemical_imaging, last modified on Oct. 26, 2013, pp. 1-10.
"Electro-optic modulator," Wikipedia, accessed at http://web.archive.org/web/20130704174600/http://en.wikipedia.org/wiki/Electro-optic_modulator, last modified on May 29, 2013, pp. 1-3.
"Full Spectrum Imaging," Wikipedia, accessed at http://web.archive.org/web/20130707073026/http://en.wikipedia.org/wiki/Full_Spectral_Imaging, last modified on Dec. 30, 2012, p. 1.
"Hyperspectral imaging," Wikipedia, accessed at http://web.archive.org/web/20140309033212/http://en.wikipedia.org/wiki/Hyperspectral_imaging, last modified on Feb. 7, 2014, pp. 1-10.
"JShakyaPsych2012Project," accessed at http://white.stanford.edu/teach/index.php/JShakyaPsych2012Project, last modified on Mar. 22, 2012, pp. 1-8.
"Principal component analysis," Wikipedia, accessed at http://web.archive.org/web/20140401053202/http://en.wikipedia.org/wiki/Principal_Component_Analysis, last modified on Mar. 31, 2014, pp. 1-21.
"French Institute for Research in Computer Science and Automation," Wikipedia, accessed at http://web.archive.org/web/20140402001700/http://en.wikipedia.org/wiki/French_Institute_for_Research_in_Computer_Science_and_Automation, last modified on Mar. 9, 2014, pp. 1-2.
"Scale-invariant feature transform," Wikipedia, accessed at http://web.archive.org/web/20130815094517/http://en.wikipedia.org/wiki/Scale-invariant_feature_transform, last modified on Aug. 14, 2013, pp. 1-14.
Bajcsy, P. and Kooper, R., "Prediction Accuracy of Color Imagery from hyperspectral Imagery," Proc. SPIE 5806, Algorithms and Technologies for Multispectral, Hyperspectral, and Ultraspectral Imagery XI, vol. 330, pp. 1-12 (Jul. 13, 2005).
Bannon, D., "Hyperspectral Imaging cubes and slices," Nature Photonics, vol. 3, No. 11, pp. 627-629 (Nov. 2009).
Geladi, P. L. M., et al., "Chapter 1: Multivariate images, Hyperspectral Imaging: Background and Equipment," in Techniques and Applications of Hyperspectral Image Analysis, pp. 1-16 ( 2007).
Holasek, R. E., et al., "HSI Mapping of Marine and Coastal Environments using the Advanced Airborne Hyperspectral Imaging System (AAHIS)," Proceedings of the SPIE, vol. 3071, pp. 169-180 (1997).
International Search Report and Written for International Application No. PCT/US2014/033106, dated Aug. 20, 2014.
Mukherjee, A., et al., "Interest Points for Hyperspectral Image Data," IEEE Transactions on GeoScience and Remote Sensing, vol. 47, Issue 3, pp. 748-760 (Mar. 2009).
Zuzak, K. J., et al., "Active DLP hyperspectral illumination: a noninvasive, in vivo, system characterization visualizing tissue oxygenation at near video rates," Anal Chem, vol. 83, No. 19, pp. 7424-7430 (Oct. 1, 2011).
Cudahy, T., et al., "Next Generation Mineral Mapping: Queensland Airborne HyMap and Satellite ASTER Surveys 2006-2008," CSIRO Exploration & Mining Report P2007 / 364, Dec. 18, 2008, 160 pages.

* cited by examiner

IDENTIFICATION SYSTEM AND METHOD

CROSS-REFERENCE TO RELATED APPLICATION

This Application is the U.S. National Stage filing under 35 U.S.C. § 371 of International Application No. PCT/US20141033106, filed an Apr. 5, 2014. The International application is hereby incorporated by reference in its entirety.

BACKGROUND

Unless otherwise indicated herein, the materials described in this section are not prior art to the claims in this application and are not admitted to be prior art by inclusion in this section.

Hyperspectral cameras can be used in areas including agriculture, mineralogy, physics, medicine and surveillance, for example, to image objects. The imaging, which uses a large range of the electromagnetic (EM) spectrum can provide spectral information regarding the object, and the spectral information can be compared to spectral signatures of known substances to identify the object.

Hyperspectral cameras may be, however, expensive and bulky, and may acquire data at very high volumes which may involve significant processing to extract information. The complexity of doing so may result in low frame rates and may limit the refresh rate or the number of images a hyperspectral camera can capture in a given time frame.

SUMMARY

In some embodiments, a system to identify at least a property of a substance located in an object or located on at least one surface of the object is generally described.

An example system includes an electromagnetic radiation (EMR) source arranged to selectively emit EMR at more than one wavelength or wavelength range to illuminate the at least one surface of the object.

The system may also include an EMR sensor arranged to sense EMR returned from the at least one surface and to use the returned EMR to provide an output signal that represents an image taken of the surface, the image including a plurality of pixels.

The system may also include a processor system arranged to compare information that is indicative of the output signal of the EMR sensor with reference information indicative of the property of the substance in a manner such that the information indicative of the output signal is compared with the reference information on a pixel by pixel basis for the plurality of pixels in the image.

The processor system may be arranged to determine that the substance is located in the object or located on the at least one surface of the object if information concerning the at least the property can be obtained as a result of the comparison of the information indicative of the output signal with the reference information.

The processor system may further be arranged to select a first wavelength or First wavelength range to illuminate the at least one surface by the EMR source, and subsequently select at least one further wavelength or further wavelength range to illuminate the at least one surface by the EMR source, wherein the selection of the at least one further wavelength or the further wavelength range is based on whether the information concerning the property is obtained as a result of use of a preceding wavelength or a preceding wavelength range for illumination of the at least one surface.

The processor system may further be arranged to compensate for an influence of ambient light on the at least one surface.

The processor system may further be arranged to compensate for motion of the object relative to the EMR sensor during illumination of the at least one surface of the object, such that the image is motion-compensated.

In some embodiments, a method to identify at least a property of a substance located in an object or located on at least one surface of the object is generally described.

An example method includes selecting a first wavelength or wavelength range. The method may include emitting EMR at the selected first wavelength or wavelength range so as to illuminate the at least one surface of the object.

The method may include receiving EMR returned from the at least one surface of the object in response to illumination of the at least one surface by the emitted EMR.

The method may include providing, using the returned EMR, an output signal that represents an image taken of the surface, the image including a plurality of pixels.

The method may include comparing information that is indicative of the output signal with reference information indicative of the property of the substance in a manner such that the information indicative of the output signal is compared with the reference information on a pixel by pixel basis for the plurality of pixels in the image, wherein a determination that the substance is located in the object or located on the at least one surface of the object is made if information concerning the at least the property can be obtained as a result of the comparison of the information indicative of the output signal with the reference information.

The method may include selecting at least one further wavelength or further wavelength range to illuminate the at least one surface of the object based on whether the information concerning the property is obtained as a result of use of a preceding wavelength or a preceding wavelength range for illumination of the at least one surface.

The method may further include compensating for an influence of ambient light on the at least one surface, and compensating for motion of the object relative to an EMR sensor at which the EMR returned from the at least one surface of the object is received during illumination of the at least one surface of the object, such that the image is motion-compensated.

In some embodiments, a non-transitory computer-readable medium that includes computer-readable instructions stored thereon that are executable by a processor is generally described.

An example non-transitory computer-readable medium is arranged such that the computer-readable instructions stored thereon are executable by a processor to perform the example method described above.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings. In the drawings:

DETAILED DESCRIPTION

Figure 1:
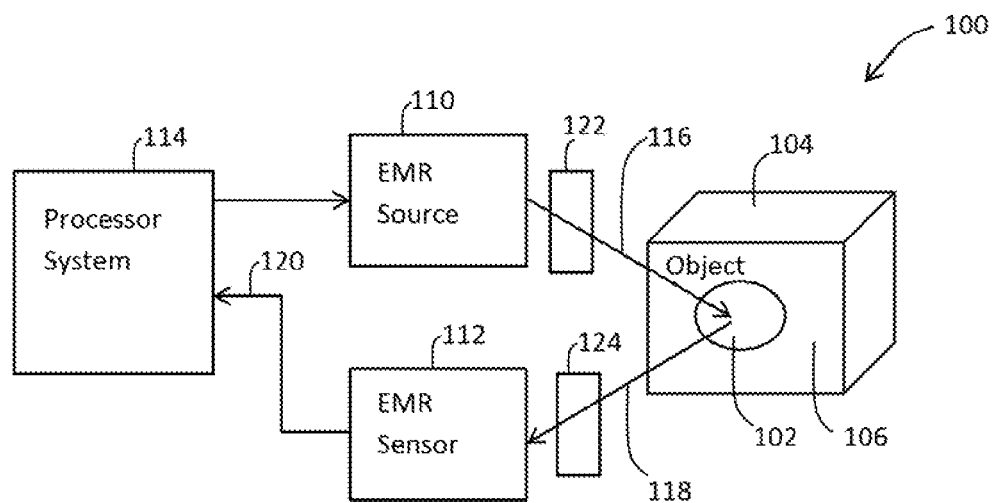
FIG. 1 is a block diagram of an example identification system.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and computer programs related to identifying a substance located in an object, or located on at least one surface of the object.

Briefly stated, a system to identify at least a property of a substance located in an object, or located on a surface of the object, may include an electromagnetic radiation (EMR) source arranged to selectively emit EMR at more than one wavelength to illuminate the surface of the object. The system may include an EMR sensor arranged to sense EMR returned from the surface and to use the returned EMR to provide an output signal that represents an image taken of the surface, the image including a plurality of pixels. The system may include a processor system arranged to compare information that is indicative of the output signal of the EMR sensor with reference information indicative of the property of the substance. The processor system may be arranged to select a first wavelength to illuminate the surface by the EMR source, and subsequently select at least one further wavelength based on whether the information concerning the property is obtained as a result of use of a preceding wavelength. The processor system may further be arranged to compensate for an influence of ambient light on the at least one surface, and may be further arranged to compensate for motion of the object relative to the EMR sensor during illumination of the at least one surface of the object, such that the image is motion-compensated.

FIG. 1 is a block diagram of an example identification system 100 that is arranged according to at least some embodiments described herein. The system 100 may be arranged to identify a property of a substance 102 located in an object 104, or located on a surface 106 of the object 104.

It will be appreciated that having the capability to identify the property of the substance can facilitate the system positively identifying the substance itself as being located in or on the object. For example, a property of the substance may be a spectral characteristic of radiation that is reflected or otherwise returned, from the substance. Identifying the spectral characteristic of radiation that is returned from the substance may facilitate positively identifying the substance.

The system 100 may include an electromagnetic radiation (EMR) source 110, an EMR sensor 112, and a processor system 114.

EMR source 110 may be arranged to selectively emit EMR 116 at more than one wavelength or wavelength range to illuminate the surface 106 of the object 104.

The EMR sensor 112 may be arranged to sense EMR 118 returned, such as by reflection, from the surface 106 and to use the returned EMR 118 to provide an output signal 120 (such as in the form of an electrical signal, wireless signal, optical signal, and/or other signal format) that represents an image taken of the surface 106 of the object 104. The image, in this example, may include a plurality of pixels.

In this example, the processor system 114 may be arranged to compare information that is indicative of the output signal 120 of the EMR sensor 112 with reference information that is indicative of the property of the substance 102. The processor system 114 may be arranged to perform the comparison in a manner such that the information indicative of the output signal 120 is compared with the reference information on a pixel by pixel basis for the plurality of pixels in the image. The processor system 114 may be arranged to determine that the substance 102 is located in the object 104, or located on the surface 106 of the object 104, if information concerning the property can be obtained as a result of the comparison of the information that is indicative of the output signal 120 with the reference information. For example, the comparison may indicate that there is a match between the information that is indicative of the output signal 120 and the reference information.

In this example, the processor system 114 may be also arranged to select a first wavelength or first wavelength range to illuminate the surface 106 by the EMR source 110, and subsequently select a further wavelength or further wavelength range to illuminate the surface 106 by the EMR source 110. The selection of the further wavelength or the further wavelength range may be based on whether the information concerning the property is obtained as a result of use of a preceding wavelength or a preceding wavelength range for illuminating the surface 106.

In one embodiment, the first wavelength or first wavelength range ma correspond to a first spectrum that can be used to identify a first group of related substances, such as a group comprising drugs. If it is determined, based on the comparison between the returned EMR 118 and reference information indicative of the first group of substances, that the substance 102 does not belong to the first group, then a second wavelength or second wavelength range that corresponds to a second spectrum that can be used to identify a second group of related substances, such as a group of explosives, can be selected and used to illuminate the surface 106. This process can continue until the group of substances has been identified.

In some embodiments, the first, second, third, etc. wavelengths or wavelength ranges can be used for identification within the same group of related substances. For instance, if the first wavelength or the first wavelength range is intending to identify drug "A", and such identification is unsuccessful, then the second wavelength or second wavelength range can be used to try to identify drug "A". This process can be repeated for all of the available wavelengths and wavelength ranges, in an attempt to identify drug "A", and then repeated again (if appropriate) to try to identify drug "B" and/or any other drug, until a match or other positive identification occurs for a particular drug type.

The first spectrum and the second spectrum (and any further spectra utilised to identify further groups of related substances can be mutually exclusive to one another. In this way, the system 100 can select further spectra with which to illuminate the surface 106 based on the result of illuminating the surface 106 with previously selected spectra rather than illuminating the surface 106 with all possible spectra in order to identify the group of the substance 102.

If it is determined, based on the comparison between the returned EMR 118 and reference information indicative of the first group, that the substance 102 belongs to the first group, then a further wavelength or further wavelength range that corresponds to a spectrum that can be used to identify one of a subset of the first group can be selected and used to illuminate the surface 106.

The subset of the first group can be determined in a manner similar to that in which the identity of the first group was determined. For example, a first subset spectrum corresponding to a first subset of the first group can be selected and used to illuminate the surface 106. If it is determined, based on the comparison between the returned EMR 118 and reference information indicative of the first subset of the first group, that the substance 102 does not belong to the first subset, then a second wavelength or second wavelength range that corresponds to a second subset spectrum that can be used to identify a second subset of the first group can be selected and used to illuminate the surface 106. This process can continue until the subset of the substance 102 has been identified.

Similar to before, the first subset spectrum and the second subset spectrum (and any further spectra utilised to identify the subset of the substance) can be mutually exclusive to one another. In this way, the system 100 can select further spectra with which to illuminate the surface 106 based on the result of illuminating the surface 106 with previously selected spectra rather than illuminating the surface 106 with all possible spectra in order to identify the subset of the substance 102.

The subsets of the first group may be different groups of drugs that share spectral reflection characteristics and/or other spectral characteristics, and the system 100 can be used to identify a further subset of an already identified subset. A subset of a group may be a particular substance.

In some embodiments, the first, second, third, etc. wavelengths or wavelength ranges can be used for identification within the same group of related substances. For instance, if the first wavelength or the first wavelength range is intending to identify drug "A", and such identification is unsuccessful, then the second wavelength or second wavelength range can be used to try to identify drug "A". This process can be repeated for all of the available wavelengths and wavelength ranges, in an attempt to identify drug "A", and then repeated again (if appropriate) to try to identify drug "B" and/or any other drug, until a match or other positive identification occurs for a particular drug type. In this manner, the various available wavelengths or wavelength ranges can be cycled through for various possible substances.

The returned EMR 118 may typically include a component of the emitted EMR 116, and a component of ambient light. In the example system 100 of FIG. 1, the processor system 114 may be arranged to compensate for an influence of ambient light on the surface 106 and/or on the returned EMR 118.

In one example, EMR that is generated by the EMR source 110 may be relatively intense and of short direction, thereby increasing the signal to noise ratio of the emitted EMR 116 to the ambient light (considering the ambient light as noise).

Further, or alternatively, the system 100 may comprise a polariser 122 arranged such that EMR generated by the EMR source 110 passes therethrough and is polarised. The system 100 may timber comprise a polarisation filter 124 arranged in front of the EMR sensor 112 so as to filter out EMR that does not have the same polarisation as EMR that has been polarised by the polariser 122, thereby improving the signal to noise ratio of the returned EMR 118 to the ambient light.

In another embodiment, the spectra of the ambient light can be determined so as to allow for the influence thereof to be removed from information that is indicative of the output signal 120 by, for example, software correction performed or controlled by processor system 114.

The spectra of the ambient tight can be determined using any appropriate method. In one example, a spectrophotometer can be used to determine the spectra of the ambient light by direct measurement. The spectra of the ambient light can also be determined indirectly, such as by performing a colour calibration measurement using a colour calibration card; providing a user of the system 100 with manual selection of ambient light spectra based on known lighting conditions (such as lighting conditions that correspond to the presence of fluorescent light, sunlight or incandescent light for example); or by using a target card having a specific reflectance spectra and determining the spectra of the ambient light based on a measurement of ambient light reflected from the target card. Other techniques or combination(s) thereof may be used.

During imaging of the surface 106, the object 104 may move, or the EMR sensor 112 may move, and/or both may move. The processor system 114 may be arranged to compensate for motion of the object 104 relative to the EMR sensor 112 when the surface 106 of the object 104 is being illuminated such that the image is motion-compensated.

The influence of such movement may be reduced by using, for example, an inertial measurement unit (which may include an accelerometer and a gyroscope) attached to, or otherwise associated with, the EMR sensor 112 to measure movement of the EMR sensor 112. Further, or alternatively, the system 100 may be arranged to determine features of an imaged scene that includes the surface 106, and to align the determined features between images of the scenes so as to compensate for movement of the object 104 and/or the EMR sensor 112.

Examples of EMR source 110 arrangements will now be described in more detail.

Figure 2:
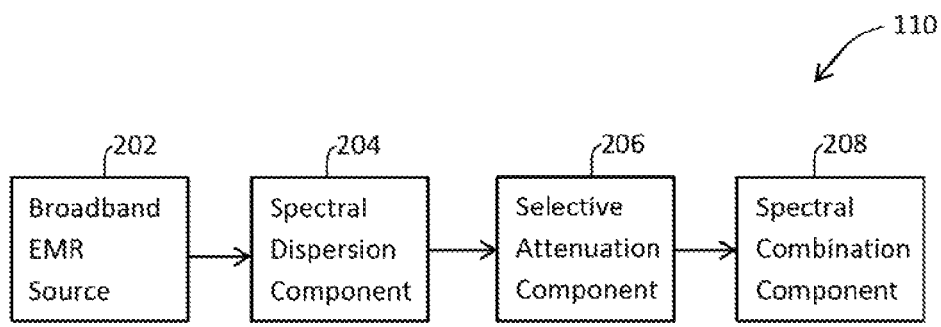
FIG. 2 is a block diagram of an example EMR source of the identification system of FIG. 1.

FIG. 2 is a block diagram of an example EMR source 110 of the identification system 100 of FIG. 1. In one example, shown in FIG. 2, the EMR source 110 may comprise a broadband EMR source 202 for generating light having a broad spectrum. The EMR source 110 may also comprise a spectral dispersion component 204 that is arranged to divide the generated broad spectrum light into its spectral components. The EMR source 110 may further comprise a selective attenuation component 206 for attenuating spectral components of the generated broad spectrum light as appropriate, and a spectral combination component 208 for recombining spectral components that were not attenuated into EMR having a specific, selected spectrum.

In the above example, the spectral dispersion component 204 may comprise a first prism, for example, a glass prism, arranged to disperse EMR generated by the broadband EMR source 202. The selective attenuation component 206 may comprise a liquid crystal display (LCD) system arranged to facilitate selective attenuation of spectral components that are directed into the LCD system. The spectral combination component 208 in this example may comprise a second prism, the second prism being substantially similar to the first prism. An output from the LCD system may be directed through the second prism and the selectively attenuated spectral components may be combined to provide the emitted EMR 116 which is used to illuminate the surface 106 of the object 104.

Alternative embodiments for producing the emitted EMR 116 are envisaged. For example, a diffraction gating can be used in place of a prism so as to provide liner spectral control, or a mico-mirror array can be used to selectively attenuate the spectral components.

The source of EMR it may not be a broadband EMR source, and a selected spectra can be generated by measuring the spectra of the EMR source 202 and then determining which bands of the spectra are to be attenuated to create the selected spectra.

In another example, the EMR source 110 may be arranged to facilitate generation of EMR having a specific, selected spectrum by temporal smearing. In this example, a pulse of light can be generated using a supercontinuum source before dispersing the pulse of light on a temporal basis, by using either material dispersion, or waveguide dispersion. The temporally dispersed pulse of light may be then passed through an electro-optic modulator so as to modulate the amplitude of the beam at that instant, and therefore the spectra of the EMR source 110.

In another example, a plurality of light sources, each having a different spectra, can be combined to generate a light source having a desired spectra. Each light source will typically provide a spectrum that is orthogonal to any other light source's spectrum. In one example, each light source produces light at a unique, discrete band.

In the example system 100, the EMR sensor 112 may be arranged to capture the image of the surface 106 of the object 104 when illuminated by the EMR source 110. The EMR sensor 112 may be a CCD/CMOS sensor that does not include a colour filter array. The image can be formed on the EMR sensor 112 using optics, and filters/diffraction gratings may not typically be used for the image sensing.

Once each image has been exposed on the EMR sensor 112, the charge count of each pixel may be digitized and output to the processor system 114. The image can now be thought of for example, as an array of numbers, stored on the processor system 114.

The processor system 114 may then process the image data to determine the identity of the substance 102. The processor system 114 may be, in this example, a computing device, such as a personal computer, arranged to carry out the processing functions of the processor system 114.

Once one or more images of the substance 102 have been obtained, using particular spectra, information concerning each pixel may be compared to known information in respect of one or more different target groups of substances and/or individual substance. For example, target groups could be groups of explosives, cocaine, cancer, or any other appropriate group of substances a user of the system 100 wants to detect.

An appropriate algorithm, for example an algorithm implemented as software running on and/or executable by the processor system 114, can be used to carry out the comparison. For example, a distance between the measured vector and each possible substance group vector can be measured, and the pixel can be assigned to the closest group.

For example, if flour has a laboratory measured vector of:
[3,5,22,1,32,−1,2,1];
(e.g., in a first image the pixel value was measured to have a value of 3, in a second image the pixel value was measured to have a value of 5 in a third image the pixel value was measured to have a value of 22, and so on)
and cocaine has a laboratory measured vector of
[4,7,14,2,32,−4,4,2];
and a pixel of an image attic substance 102 taken by the system 100 is determined to have a vector of:
then the distance, using a Euclidian measure from the flour vector, is:
$(5-3)^2+(6-5)^2+(14-22)^2+(3-1)^2+(34-32)^2+(-5+1)^2+(3-2)^2+(2-1)^2=4+1+64+4+4+16+1+1=95;$
and the distance, using a Euclidian measure from the cocaine vector, is:
$(5-4)^2+(6-7)^2+(14-14)^2+(3-2)^2+(34-32)^2+(-5+4)^2+(3-4)^2+(2-2)^2=1+1+0+1+4+1+1+0=9.$ From the above, because the pixel vector is closer to the vector which corresponds to cocaine, it can be concluded that the contents of the pixel of the image obtained using the system 100 may be more likely to be cocaine than flour.

This process may be carried out for each pixel in the image, and the image captured by the system 100 can then be shown to an operator, and an alarm can be raised if necessary.

In this example, the system 100 may be arranged to select a spectra to illuminate the surface 106 of the object 104 based on an analysis of an image of the surface 106 of the object 104 that has been captured white being illuminated by a previously selected spectra.

The system 100, and in particular the processor system 114, can be arranged to perform the spectra selection in an appropriate way, such as by using a binary space partitioning tree, which can facilitate determination by the system 100 of the identity of the substance 102 from a number of substances that may be present in the image. Using a binary space tree as a tool in selecting the spectra, rather than linearly searching a set of possible substances, for example, can reduce the time taken to identify the substance 102.

In this particular example, nodes of the binary space tree may correspond to the spectra of substances of interest that may possibly be observed in the image, and hyperplanes that separate nodes of the binary space tree may correspond to the illumination spectra.

At each stage of illumination, the processor system 114 may decide which spectra to use based on what the system 100 has observed so far and may use the binary space tree to determine which spectra (corresponding to a particular hyperplane of the binary space tree), to use next to most efficiently determine the identity of the substance 102 in the image.

As a result of selecting a spectrum for illuminating the object 104 based on analysis of an image captured using a previously selected spectrum, the total imaging tune may be a function of the number of different substances in the image, rather than the number of possible different substances of interest that may be observed. The system 100 can, therefore, identify the substance 102 in a shorter period of time compared to if an approach of linearly searching a set of possible substances is used. Consequently, the system 100 can operate at a higher frame rate, and can be used to detect substances more efficiently compared to if sonic other approach has been taken.

For example, using a method of linearly searching a set of possible substances one at a time may be sufficient if a user of the system 100 has some knowledge of what substances the user is attempting to detect, for example one of cocaine, semtex, ricin, ammonium nitrate, or baking flour. However, using the such method, if a user of the system 100 wants to detect one of the five different substances mentioned, the system 100 may take five different sets of images (for example 5*20 images), to linearly determine if any of the substances of interest are in the scene. Under this method, because imaging time may be proportional or otherwise related to the number of substances of interest, it can be seen that there may be a limit to the number of substances of interest which may be efficiently detected.

In comparison, the system 100 of one embodiment may be arranged to determine the identity of the substance 102 by illuminating the surface 106 of the object 104 with spectra that have been selected based on the result of analysing images captured when the surface 106 of the object 104 has been illuminated with previously selected spectra. In this example, each substance, or group of substances, may have a spectral characteristic that is mutually exclusive to the other substances, or group of substances. For example, there may be a known spectrum for the group of explosive substances that may be present in one or many forms of explosives, but that is not present in the group of drug substances. Further, each type of explosive substance may have a spectrum that is not present in every type of explosive substance.

If as a result of illuminating the surface 106 with a spectrum that is specific to the group of explosive substances, it is determined that no explosive substances are present, the system 100 may select a different spectrum that is exclusive to a further group of substances, for example the group of drug substances, until one spectrum is identified that is unique in that group of substances.

Once a particular group of substances has been identified, the system 100 may then select spectra that are present in substances of the identified group of substances until the actual substance is identified.

Figure 3:
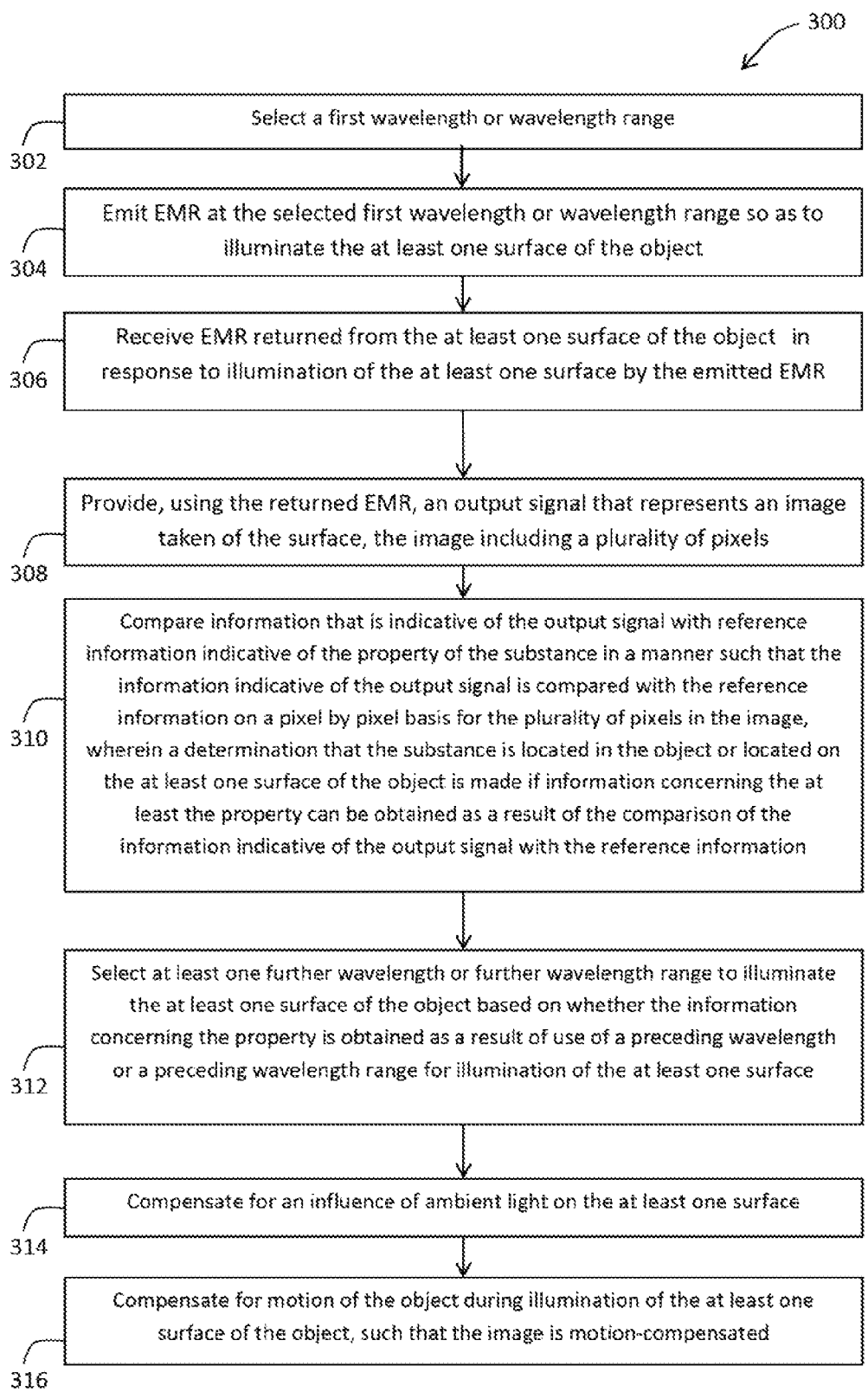
FIG. 3 is an example identification method.

FIG. 3 is an example identification method. More specifically, a method 300 to identify the substance 102 using the system 100 will now be described with reference to FIG. 3.

In some examples, the process in FIG. 3 could be implemented using system 100 discussed above. An example process may include one or more operations, actions, or functions as illustrated by one or more of blocks 302-316. Although illustrated as discrete blocks, various blocks may be divided into additional blocks, combined into fewer blocks, or eliminated, depending on the particular implementation. Blocks may be supplemented with additional blocks representing other operations, actions, or functions.

The example method 300 may include a block 302 of selecting a first wavelength or wavelength range. In a block 304, which may follow the block 302, the EMR source 110 may emit EMR at the selected first wavelength or wavelength range so as to illuminate at least one surface 106 of the object 104. In a block 306, which may follow the block 304, EMR returned from the at least one surface 106 of the object 104 may be received by the EMR sensor 112 in response to illumination of the at least one surface by the emitted EMR.

The output signal 120, which may represent an image taken of the surface 106, may be provided in a block 308 that may follow the block 306. In the block 308, the returned EMR may be used to provide the output signal 120. The image may typically include a plurality of pixels.

In a block 310, which may fellow the block 308, information that is indicative of the output signal 120 may be compared with reference information that is indicative of the property of the substance 102. The comparison of the block 310 may be performed in a manner such that the information indicative of the output signal 120 is compared with the reference information on a pixel by pixel basis for the plurality of pixels in the image.

The block 310 may be performed by the processor system 114 and, in this example, the processor system 114 may be arranged to determine that the substance 102 is located in the object 104, or located on the surface 106 of the object 104. If information concerning the property can be obtained as a result of the comparison of the information indicative of the output signal 120 with the reference information.

In a block 312, which may follow the block 310, at least one further wavelength or further wavelength range may be selected to illuminate the surface 106 of the object 104 by the EMR source 110 based on whether the information concerning the property is obtained as a result of use of a preceding wavelength or a preceding wavelength range for illumination of the surface 106.

A block 314 of the method 300 may follow the block 312 and may include compensating for an influence of ambient light on the surface 106 of the object 104.

A block 316 may follow the block 314 and may include compensating for motion of the object during illumination of the at least one surface of the object, such that the image is motion-compensated.

While security applications have been described by way of example, the system 100 can be used in other appropriate applications, for example medical segmentation, wherein the system 100 may be arranged to determine what parts of a scene are liver, kidney, connective tissue, biofilm, etc. The object 104 may include a person or a piece of clothing of the person. Further, the substance 102 may include, in solid form or in liquid form, at least one of a drug, an explosive, a radioactive material, or a food product.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. This disclosure is not limited to particular methods, reagents, compounds, compositions or biological systems, which can, of course, vary. The used herein is for the purpose of describing particular embodiments only, and is not intended to be limiting.

In an illustrative embodiment, any of the operations, processes, etc. described herein can be implemented as computer-readable instructions stored on a non-transitory computer-readable medium. The computer-readable instructions can be executed by a processor of a mobile unit, a network element, and/or any other computing device.

Figure 4:
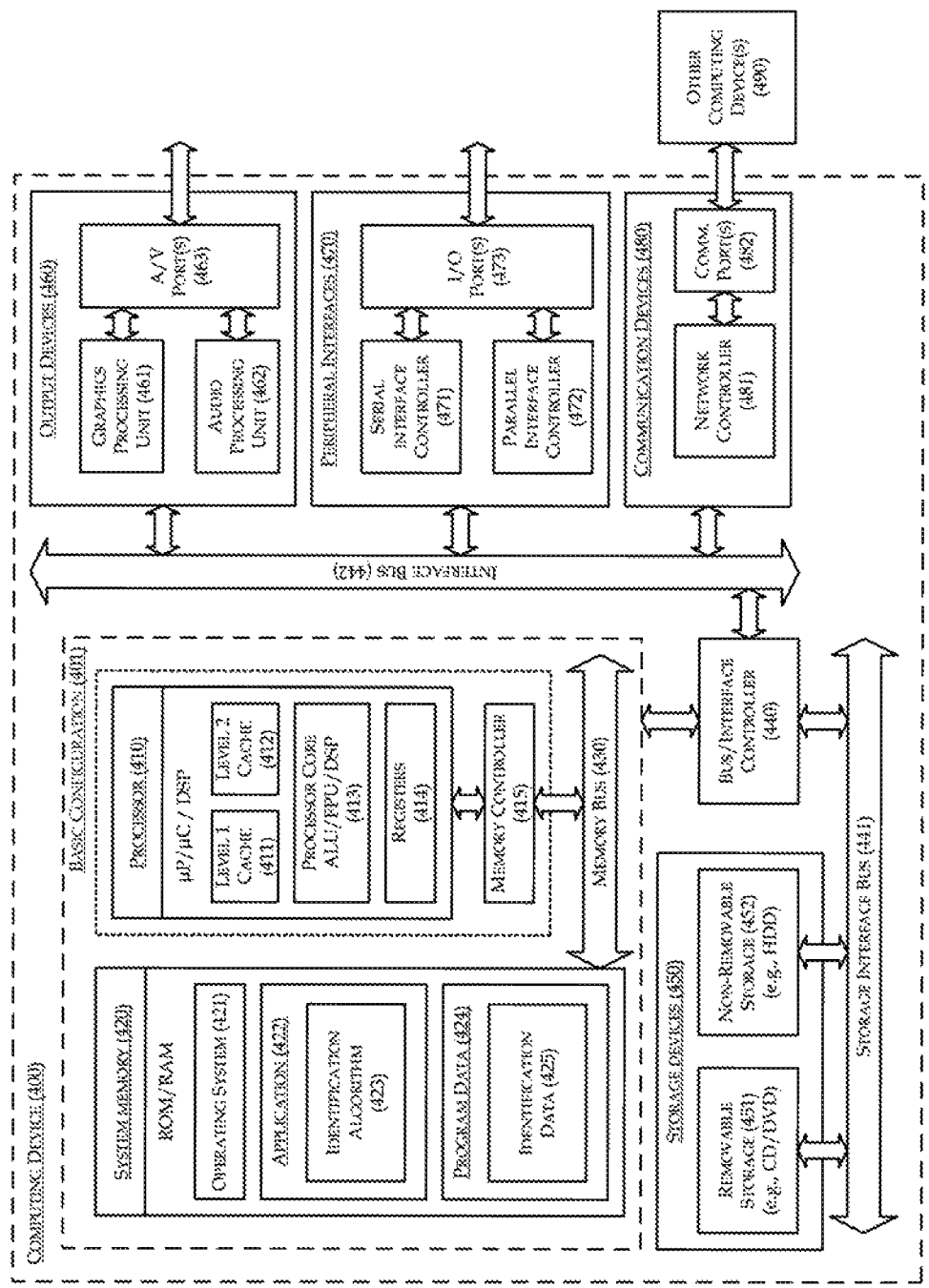
FIG. 4 is a block diagram illustrating an example computing device that is arranged to process images in connection with substance identification, all arranged according to at least some embodiments presented herein.

FIG. 4 shows an example of one such computing device. Specifically, FIG. 4 is a block diagram illustrating an example computing device 400 that is arranged to process images in connection with substance identification in accordance with the present disclosure. In one embodiment, at least some of the elements of the system 100 of FIG. 1 can be implemented in or by the computing device 400 of FIG. 4.

In a very basic configuration 401, computing device 400 typically includes one or more processors 410 and system memory 420. A memory bus 430 can be used for communicating between the processor 410 and the system memory 420. In one embodiment, the processor system 114 of FIG. 1 can be implemented in whole or in part by the processor 410 of FIG. 4.

Depending on the desired configuration, processor 410 can be of any type including but not limited to a microprocessor (μP), a microcontroller (μC), a digital signal processor (DSP), or any combination thereof. Processor 410 can include one or more levels of caching, such as a level one cache 411 and a level two cache 412, a processor core 413, and registers 414. The processor core 413 can include an arithmetic logic unit (ALU), a floating point unit (FPU), a digital signal processing core (DSP core), or any combination thereof. A memory controller 415 can also be used with the processor 410, or in some implementations, the memory controller 415 can be an internal part of the processor 410.

Depending on the desired configuration, the system memory 420 can be of any type including but not limited to volatile memory (such as RAM), non-volatile memory such as ROM, flash memory, etc.) or any combination thereof. System memory 420 typically includes an operating system 421, one or more applications 422, and program data 424. Application 422 may include an identification algorithm 423 that may cooperate with the processor 410 to perform one or more of control the EMR 116 to illuminate the object 104, process the returned EMR 118 to provide the output signal 120, process images(s) represented by the output signal 120 (including comparing information contained in or represented by the output signal 120 with reference information), perform the binary space tree operations, compensate for ambient light and motion, and/or other operations described above that pertain to illumination and identification of a substance in or on the object 104. Program Data 424 may include identification data 425 that is usable for performing the identification algorithm 423, including but not limited to reference information, vector values, binary space tree values, settings for EMR spectra, calculation results, and/or other data. In some embodiments, application 422 can be arranged to operate with program data 924 on an operating system 421. such that the illumination and identification as described above are performed. This described basic configuration is illustrated in FIG. 4 by those components within dashed line.

Computing device 400 can have additional features or functionality, and additional interfaces to facilitate communications between the basic configuration 401 and any required devices and interfaces. For example, a bus/interface controller 440 can be used to facilitate communications between the basic configuration 401 and one or more data storage devices 450 via a storage interface bus 441. The data storage devices 450 can be removable storage devices 451, non-removable storage devices 452, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSDs), and tape drives to name a few. Example computer storage media can include volatile and nonvolatile, removable and non-removable media implemented in any method or technology for storage of information, such as computer readable instructions, data structures, program modules, or other data.

System memory 420, removable storage 451 and non-removable storage 452 are all examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which can be used to store the desired information and which can be accessed by computing device 400. Any such computer storage media can be part of computing device 400.

Computing device 400 can also include an interface bus 442 for facilitating communication from various interface devices (e.g., output interfaces, peripheral interfaces, and communication interfaces) to the basic configuration 401 via the bus/interface controller 440. Example output devices 460 include a graphics processing unit 461 and an audio processing unit 462, which can be configured to communicate to various external devices such as a display or speakers via one or more A/V ports 463. Example peripheral interfaces 470 include a serial interface controller 471 or a parallel interface controller 472, which can be configured to communicate with external devices such as input devices (e.g., keyboard, mouse, pen, voice input device, touch input device, etc.) or other peripheral devices (e.g., printer, scanner, etc.) via one or more I/O ports 473. An example communication device 480 includes a network controller 481, which can be arranged to facilitate communications with one or more other computing devices 490 over a network communication via one or more communication ports 482. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media as used herein can include both storage media and communication media.

Computing device 400 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 400 can also be implemented as a personal computer including both laptop computer and non-laptop computer configurations.

The use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; it flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and designing the circuitry and/or writing the code for the software and/or firmware would be possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a compact disc (CD), a digital versatile disc (DVD), a digital tape, a computer memory, etc; and a transmission type medium such as a digital and/or an analog communication medium (e.g., a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as of touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained, within, or connected with, different other components. Such depicted architectures are merely examples, and in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as associated with each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interact able and/or wirelessly interacting components and/or logically interacting and/or logically interactable table components.

With respect to the use of substantially any plural and/or singular terms herein, those having skill in the art can translate from the plural to the singular and/or from the singular to the plural as is appropriate to the context and for application. The various singular/plural permutations may be expressly set forth herein for sake of clarity.

It will be understood by those within the art that, in general, terms used herein, and especially in the appended claims (e.g., bodies of the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing front the scope and spirit of the present disclosure. Accordingly, the various embodiments disclosed herein are not intended to be limiting, with the true scope and spirit being indicated by the following.

What is claimed is:

1. A system to identify a property of a substance located in one from a set of: an object and on at least one surface of the object, the system comprising:
    an electromagnetic radiation (EMR) source arranged to emit EMR at more than one from a set of: a wavelength and a wavelength range to illuminate the at least one surface of the object;
    an EMR sensor arranged to sense EMR returned from the at least one surface and to use the renimed EMR to provide an output signal that represents an image taken of the at least one surface, wherein the image includes a plurality of pixels; and
    a processor system arranged to compare information that is indicative of the output signal of the EMR sensor with reference information indicative of the property of the substance in a manner such that the information indicative of the output signal is compared with the reference information on a pixel by pixel basis for the plurality of pixels in the image, wherein the processor system is arranged to determine that the substance is located in the one from the set of: the object and on the at least one surface of the object if information concerning the property can be obtained as a result of the comparison of the information indicative of the output signal with the reference information, and wherein the processor system is further arranged to:
    select one from a set of: a first wavelength and a first wavelength range to illuminate the at least one surface by the PMR source, and subsequently select one from a set of: a second wavelength and a second wavelength range to illuminate the at least one surface by the EMR source, wherein the selection of the one from the set of: the second wavelength and the second wavelength range is based on whether the information concerning the property is obtained as a result of use of the one from the set of: the first wavelength and the first wavelength range for the illumination of the at least one surface;
    compensate for an influence of ambient light on the at least one surface through a use of the EMR sensor, wherein the EMR sensor is arranged to determine a spectrum of the ambient light from a color calibration measurement;
    filter at least a portion of the spectrum of the ambient light from information that is indicative of the EMR returned from the at least one surface: and
    compensate for motion of the object relative to the EMR sensor during the illumination of the at least one surface of the object, such that the image is motion-compensated.

2. The system of claim 1, wherein: the one from the set of the first wavelength and the first wavelength range corresponds to a first spectrum that can be used to identify a first group of related substances, and if it is determined, based on a comparison between the information that is indicative of the output signal of the EMR sensor and reference information indicative of a property of the first group of the related substances, that the substance does not belong to the first group of the related substances, then the processor system is arranged to select the one from the set of: the second wavelength and the second wavelength range that corresponds to a second spectrum that can be used to identify a second group of related substances to illuminate the at least one surface.

3. The system of claim 1, wherein if it is determined, based on a comparison between the information that is indicative of the output signal of the EMR sensor and reference information indicative of a property of a first group of related substances, that the substance belongs to the first group of the related substances, then the processor system is arranged to select one from a set of: a third wavelength and a third wavelength range that corresponds to a first subset spectrum that can be used to identify one of a subset of the first group of the related substances to illuminate the at least one surface.

4. The system of claim 3, wherein if, in response to illumination of the at least one surface of the object with the first subset spectrum, it is determined, based on acomparison between the information that is indicative of the output signal of the EMR sensor and reference information indicative of a first subset of the first group of the related substances, that the substance does not belong to the first subset of the first group of the related substances, then the processor system is arranged to select the one from the set of: the second wavelength and the second wavelength range that corresponds to a second subset spectrum that can be used to identify a second subset of the first group of the related substances.

5. The system of claim 1, wherein, to compensate for the influence of the ambient light, the processor system is arranged to control the EMR source such that the influence of ambient light returned from the at least one surface is adjusted, compared to one from a set of: a selected wavelength and a selected wavelength range generated by the EMR source, and returned from the at least one surface.

6. The system of claim 5, wherein the EMR source is arranged to generate the one from the set of: the selected wavelength and the selected wavelength range to have an intensity that is greater than that of the ambient light.

7. The system of claim 5, further comprising: a polariser that is arranged to polarise at least one from the set of: the selected wavelength and the selected wavelength range; and a filter that is arranged to filter EMR that has a different polarisation than that of the at least one from the set of: the polarised wavelength and the polarised wavelength range, prior to the EMR being received by the EMR sensor.

8. The system of claim 1, wherein the processor system is arranged to determine the spectrum of the ambient light by determination of a spectrum of EMR returned from an object having a known reflectance characteristic.

9. The system of claim 1, wherein to compensate for the motion of the object, the processor system is arranged to determine a movement of the at least one surface of the object relative to the EMR sensor to correct the output signal, based on the EMR as received by the EMR sensor over a period of time while the at least one surface moves.

10. The system of claim 1, further comprising an inertial movement unit, wherein the inertial movement unit, is associated, with one from a set of:
the object and the EMR sensor and is arranged to determine a relative movement of the at least one surface of the object and the EMR sensor.

11. The system of claim 1, wherein the EMR sensor includes an image sensor.

12. The system of claim 11, wherein the image sensor includes one from a set of: a charge-coupled device (CCD) sensor and a complementary metal-oxide-semiconductor (CMOS) sensor.

13. A method to identify a property of a substance located in one from a set of: an object and on at least one surface of the object, the method comprising:
selecting one from a set of: a first wavelength and a first wavelength range;
emitting electromagnetic radiation (EMR) at the selected one from the set of: the first wavelength and the first wavelength range to illuminate the at least one surface of the object;
receiving EMR returned from the at least one surface of the object in response to the illumination of the at least one surface by the emitted EMR;
providing, using the returned EMR, an output signal that represents an image taken of the at least one surface, wherein the image includes a plurality of pixels;
comparing information that is indicative of the output signal with reference information indicative of the property of the substance in a manner such that the information indicative of the output signal is compared with the reference information on a pixel by pixel basis for the plurality of pixels in the image, wherein a determination that the substance is located in the one from the set of: the object and on the at least one surface of the object is made if information concerning the property can be obtained as a result of the comparison of the information indicative of the output signal with the reference information;
selecting at least one from a set of: a second wavelength and a second wavelength range to illuminate the at least one surface of the object based on whether the information concerning the property is obtained as a result of use of the one from the set of: the first wavelength and the first wavelength range for the illumination of the at least one surface;
compensating for an influence of ambient light on the at least one surface through use of an EMR sensor, wherein the EMR sensor is arranged to determine a spectrum of the ambient light from a color calibration measurement:
filtering at least a portion of the spectrum of the ambient light from information that is indicative of the EMR returned from the at least one surface; and
compensating for motion of the object relative to the EMR sensor at which EMR returned from the at least one surface of the object is received during the illumination of the at least one surface of the object, such that tho image is motion-compensated.

14. The method of claim 13, further comprising selecting at least one from a set of: a third wavelength and a third wavelength range based on binary space partitioning of a binary space, wherein the binary space comprises a plurality of nodes and hypetplanes that separate nodes of the plurality of nodes, and wherein each node of the binary space is indicative of an EMR spectrum associated with a known substance, and each hyperplane of the binary space is indicative of one from a set of: a wavelength and a wavelength range that is selectable.

15. The method of claim 14, wherein: selecting the one from the set of: the third wavelength and the third wavelength range is based on a binary space tree, the binary space tree comprises the plurality of nodes and the hyperplanes that separate the nodes of the plurality of nodes,
each node of the binary space tree comprises informa ion that is indicative of the EMR spectrum associated with the known substance, and
each hyperplane of the binary space tree comprises information that is indicative of the one from the set of: the wavelength and the wavelength range that is selectable.

16. The method of claim 13, wherein compensating for the influence of the ambient light comprises controlling the emission of the EMR such that the influence of the ambient light returned from the at least one surface is adjusted compared to one from a set of: a selected wavelength and a selected wavelength range of the EMR emitted and subsequently returned from the at least one surface.

17. The method of claim 16, wherein compensating for the influence of the ambient light comprises:
polarising the emitted EMR; and
filtering EMR that has a polarisation that is different than that of the polarised EMR, prior to the EMR being received.

18. The method of claim 13, further comprising determining a movement of the at least one surface of the object relative to the EMR sensor by:
comparing at least one feature of received EMR returned from the at least one surface at a first time with the at least one feature of received EMR returned from the at least one surface at a second time.

19. The method of claim 13, wherein the emitted EMR is visible EMR.

* * * * *

UNITED STATES PATENT AND TRADEMARK OFFICE
CERTIFICATE OF CORRECTION

PATENT NO. : 9,870,515 B2
APPLICATION NO. : 15/037329
DATED : January 16, 2018
INVENTOR(S) : Cooke It is certified that error appears in the above-identified patent and that said Letters Patent is hereby corrected as shown below:

On the Title Page

In Item (57), under "ABSTRACT", in Column 2, Line 1, delete "identity" and insert -- identify --, therefor.

In Item (57), under "ABSTRACT", in Column 2, Line 19, delete "fur" and insert -- for --, therefor.

In the Specification

In Column 1, Lines 7-8, delete "PCT/US20141033106, filed an" and insert -- PCT/US2014/033106, filed on --, therefor.

In Column 1, Line 22, delete "spectrum can" and insert -- spectrum, can --, therefor.

In Column 1, Line 61, delete "or First" and insert -- or first --, therefor.

In Column 3, Line 21, delete "hereof In" and insert -- hereof. In --, therefor.

In Column 4, Lines 2-3, delete "reflected or" and insert -- reflected, or --, therefor.

In Column 4, Line 9, delete "EMR" and insert -- The EMR --, therefor.

In Column 4, Line 47, delete "ma" and insert -- may --, therefor.

In Column 5, Line 6, delete "substances can" and insert -- substances) can --, therefor.

In Column 6, Line 9, delete "timber" and insert -- further --, therefor.

In Column 6, Line 20, delete "tight" and insert -- light --, therefor.

Signed and Sealed this
Twelfth Day of June, 2018

Andrei Iancu
*Director of the United States Patent and Trademark Office*

CERTIFICATE OF CORRECTION (continued)
U.S. Pat. No. 9,870,515 B2

In Column 7, Line 14, delete "gating" and insert -- grating --, therefor.

In Column 7, Line 15, delete "liner" and insert -- finer --, therefor.

In Column 7, Line 18, delete "EMR it may" and insert -- EMR may --, therefor.

In Column 7, Line 49, delete "thought of" and insert -- thought, of --, therefor.

In Column 8, Line 7, delete "5 in" and insert -- 5, in --, therefor.

In Column 8, Line 9, delete "vector of" and insert -- vector of: --, therefor.

In Column 8, Line 11, delete "attic" and insert -- of the --, therefor.

In Column 8, Line 13, delete "vector of:" and insert -- vector of: [5,6,14,3,34,-5,3,2]; --, therefor.

In Column 8, Line 33, delete "white" and insert -- while --, therefor.

In Column 8, Line 58, delete "tune" and insert -- time --, therefor.

In Column 8, Line 66, delete "sonic" and insert -- some --, therefor.

In Column 9, Line 31, delete "If as" and insert -- If, as --, therefor.

In Column 10, Line 3, delete "fellow" and insert -- follow --, therefor.

In Column 10, Lines 14-15, delete "104. If" and insert -- 104, if --, therefor.

In Column 11, Line 26, delete "memory such" and insert -- memory (such --, therefor.

In Column 11, Line 32, delete "of control" and insert -- of: control --, therefor.

In Column 11, Line 34, delete "images(s)" and insert -- image(s) --, therefor.

In Column 11, Line 47, delete "421. such" and insert -- 421 such --, therefor.

In Column 13, Line 1, delete "vehicle; it" and insert -- vehicle; if --, therefor.

In Column 13, Line 39, delete "etc;" and insert -- etc.; --, therefor.

In Column 13, Line 57, delete "as of" and insert -- as a --, therefor.

In Column 13, Line 66, delete "contained, within," and insert -- contained within, --, therefor.

In Column 14, Line 7, delete "associated with" and insert -- "associated with" --, therefor.

CERTIFICATE OF CORRECTION (continued)
U.S. Pat. No. 9,870,515 B2

In Column 14, Line 14, delete "operably couplable" to" and insert -- "operably couplable", to --, therefor.

In Column 14, Line 18, delete "interact able" and insert -- interactable --, therefor.

In Column 14, Lines 19-20, delete "interactable table components." and insert -- interactable components. --, therefor.

In Column 14, Line 24, delete "and for" and insert -- and/or --, therefor.

In Column 14, Line 29, delete "claims are" and insert -- claims) are --, therefor.

In Column 15, Line 1, delete "haying" and insert -- having --, therefor.

In Column 15, Line 39, delete "front" and insert -- from --, therefor.

In Column 15, Line 42, delete "following." and insert -- following claims. --, therefor.

In the Claims

In Column 15, Line 52, in Claim 1, delete "renimed" and insert -- returned --, therefor.

In Column 16, Line 5, in Claim 1, delete "PMR" and insert -- EMR --, therefor.

In Column 16, Line 22, in Claim 1, delete "surface: and" and insert -- surface; and --, therefor.

In Column 16, Lines 27-28, in Claim 2, delete "set of the" and insert -- set of: the --, therefor.

In Column 16, Line 54, in Claim 4, delete "acomparison" and insert -- a comparison --, therefor.

In Column 17, Lines 27-28, in Claim 10, delete "unit, is associated, with" and insert -- unit is associated with --, therefor.

In Column 18, Line 12, in Claim 13, delete "measurement:" and insert -- measurement; --, therefor.

In Column 18, Line 17, in Claim 13, delete "which EMR" and insert -- which the EMR --, therefor.

In Column 18, Line 20, in Claim 13, delete "tho" and insert -- the --, therefor.

In Column 18, Line 25, in Claim 14, delete "hypetplanes" and insert -- hyperplanes --, therefor.

In Column 18, Line 36, in Claim 15, delete "informa ion" and insert -- information --, therefor.